(12) United States Patent
Rizzolo

(10) Patent No.: US 11,197,677 B2
(45) Date of Patent: Dec. 14, 2021

(54) SLOW BLOOD VESSEL OCCLUSION APPARATUS

(71) Applicant: Richard A Rizzolo, Ukiah, CA (US)

(72) Inventor: Richard A Rizzolo, Ukiah, CA (US)

( * ) Notice: Subject to any disclaimer, the term of this patent is extended or adjusted under 35 U.S.C. 154(b) by 238 days.

(21) Appl. No.: 16/659,976

(22) Filed: Oct. 22, 2019

(65) Prior Publication Data

US 2020/0046358 A1 Feb. 13, 2020

Related U.S. Application Data

(62) Division of application No. 15/863,187, filed on Jan. 5, 2018, now Pat. No. 10,548,604.

(51) Int. Cl.
*A61B 17/12* (2006.01)
*A61L 31/10* (2006.01)
(Continued)

(52) U.S. Cl.
CPC ........ *A61B 17/12* (2013.01); *A61B 17/12009* (2013.01); *A61B 17/1325* (2013.01); *A61D 1/00* (2013.01); *A61L 31/022* (2013.01); *A61L 31/048* (2013.01); *A61L 31/06* (2013.01); *A61L 31/10* (2013.01); *A61B 2017/00898* (2013.01); *A61B 2017/00942* (2013.01); *A61B 2017/00951* (2013.01); *A61B 2017/00964* (2013.01);
(Continued)

(58) Field of Classification Search
CPC ........... A61B 2017/00778; A61B 2017/00893; A61B 2017/00898; A61B 2017/00004; A61B 2017/00597; A61B 2017/12004; A61B 2017/00951; A61B 2017/00964; A61B 17/0057; A61B 17/12; A61B 17/12009; A61B 17/12013; A61B 17/1325; A61B 5/02233; A61L 31/06; A61L 31/10; A61L 31/041; A61L 31/048; A61L 31/145; A61L 31/022; A61L 27/18; A61L 27/52

See application file for complete search history.

(56) References Cited

U.S. PATENT DOCUMENTS 5,509,888 A * 4/1996 Miller .................. A61F 2/0036
600/29
6,171,298 B1 * 1/2001 Matsuura .............. A61L 17/145
604/891.1

(Continued)

*Primary Examiner* — Wade Miles
*Assistant Examiner* — Mikail A Mannan
(74) *Attorney, Agent, or Firm* — Donald R. Boys; Central Coast Patent Agency LLC

(57) ABSTRACT

A method for occluding a blood vessel has steps for encasing a semi-rigid, circular plastic ring, open at one point, in silicon material, forming a bladder along an inside diameter of the silicon material, placing a mixture of sodium and potassium salts and polyacrylamide granules in the bladder, closing and sealing the bladder, forming a pair of opposed stirrups on an outside diameter of the silicon material, spreading the encased plastic ring by the stirrups accomplishing an opening through the ring of an extent enabling the ring to be placed over a blood vessel, placing the encased plastic ring over the blood vessel, releasing the stirrup, allowing the ring and bladder to close around the blood vessel, such that the bladder, constrained by the ring from expanding outward, absorbing moisture by osmosis over time, expands inward, and over a time t fully occludes the blood vessel.

4 Claims, 4 Drawing Sheets

(51) Int. Cl.
*A61B 17/132* (2006.01)
*A61L 31/02* (2006.01)
*A61L 31/06* (2006.01)
*A61L 31/04* (2006.01)
*A61D 1/00* (2006.01)
*A61B 17/00* (2006.01)
*A61B 90/00* (2016.01)

(52) U.S. Cl.
CPC ............... *A61B 2017/12004* (2013.01); *A61B 2090/3966* (2016.02)

(56) References Cited

U.S. PATENT DOCUMENTS

| | | | | |
|---|---|---|---|---|
| 8,734,318 | B2 * | 5/2014 | Forsell | A61F 2/0036 |
| | | | | 600/30 |
| 2004/0138684 | A1 * | 7/2004 | Eton | A61B 17/12 |
| | | | | 606/158 |
| 2014/0066967 | A1 * | 3/2014 | Levy | A61M 31/002 |
| | | | | 606/191 |
| 2016/0121088 | A1 * | 5/2016 | Fox | A61M 29/00 |
| | | | | 606/199 |
| 2016/0199629 | A1 * | 7/2016 | Jackson | A61B 90/02 |
| | | | | 606/192 |
| 2017/0303928 | A1 * | 10/2017 | Cazenave | A61B 17/12 |
| 2018/0035994 | A1 * | 2/2018 | Gharibi Loron | A61B 17/02 |

* cited by examiner

Section A-A

SLOW BLOOD VESSEL OCCLUSION APPARATUS

CROSS REFERENCE TO RELATED DOCUMENTS

The present application is a divisional application of co-pending U.S. application Ser. No. 15/863,187, filed Jan. 5, 2018. All disclosure of the parent application is incorporated herein at least by reference.

BACKGROUND OF THE INVENTION

1. Field of the Invention

The present invention is in the field of medical devices and pertains more particularly to methods and apparatus for effecting slow occlusion of a blood vessel in treatment of extrahepatic portosystemic shunts affecting small animals.

2. Discussion of the State of the Art

Portosystemic shunts are common congenital vascular anomalies affecting small animals, more particularly, canines and felines patients. Congenital portosystemic shunt (PSS) may be caused by the failure of the fetal circulatory system of the liver to change. Normally, the blood from the placenta bypasses the liver and goes into circulation via the ductus *venosus*, a blood vessel found in the fetus. A failure of the ductus *venosus* to close causes an intrahepatic shunt, while extrahepatic shunts are usually a developmental abnormality of the vitelline veins, which connect the portal vein to the caudal vena cava. In animals with PSS, the blood from the intestines only partly goes through the liver, and the rest mixes into general circulation. Therefore, toxins like ammonia are not efficiently cleared by the liver. Most commonly, extrahepatic shunts are found connecting the portal vein or left gastric vein to the caudal vena cava.

The inventor is aware of venous slow-occlusion devices such as the Ameroid constrictor and cellophane band, which are utilized for surgical attenuation of portosystemic shunts. However, these devices work by causing thrombosis and fibrosis (tissue integration) which cannot be reliably controlled over time due to different reactions in different patients.

Therefore, what is clearly needed is a slow-occlusion apparatus for animals that works reliably to close a vessel within and at the culmination of a prescribed time period.

BRIEF SUMMARY OF THE INVENTION

In one embodiment of the invention a method is provided for occluding a blood vessel, comprising steps of encasing a semi-rigid, circular plastic ring, open at one point of a circumference, in silicon material, forming a bladder along an inside diameter of the silicon material encasing the plastic ring, placing a mixture of sodium and potassium salts and polyacrylamide granules in the bladder, and closing and sealing the bladder, forming a pair of opposed stirrups on an outside diameter of the silicon material encasing the plastic ring, spreading the encased plastic ring by the stirrups to an extent that an opening is accomplished through the ring of an extent enabling the ring to be placed over a blood vessel to be occluded, placing the encased plastic ring over the blood vessel, releasing the stirrup, allowing the ring and bladder to close around the blood vessel, such that the bladder, constrained by the ring from expanding outward, absorbing moisture by osmosis over time, expands inward, and over a time t fully occludes the blood vessel.

In one embodiment the ratio amounts of materials in the silicone bladder change time t. Also, in one embodiment the ratios are controlled to result in t=six weeks. And in one embodiment the blood vessel is a portosystemic shunt.

DETAILED DESCRIPTION OF THE INVENTION

In various embodiments described in enabling detail herein, the inventors provide a unique slow-occlusion apparatus to treat portosystemic shunts in animals, wherein the occlusion time period is reliably predicted and accommodated by the apparatus. The present invention is described in enabling detail using the following examples, which may describe more than one relevant embodiment falling within the scope of the present invention.

Figure 1:
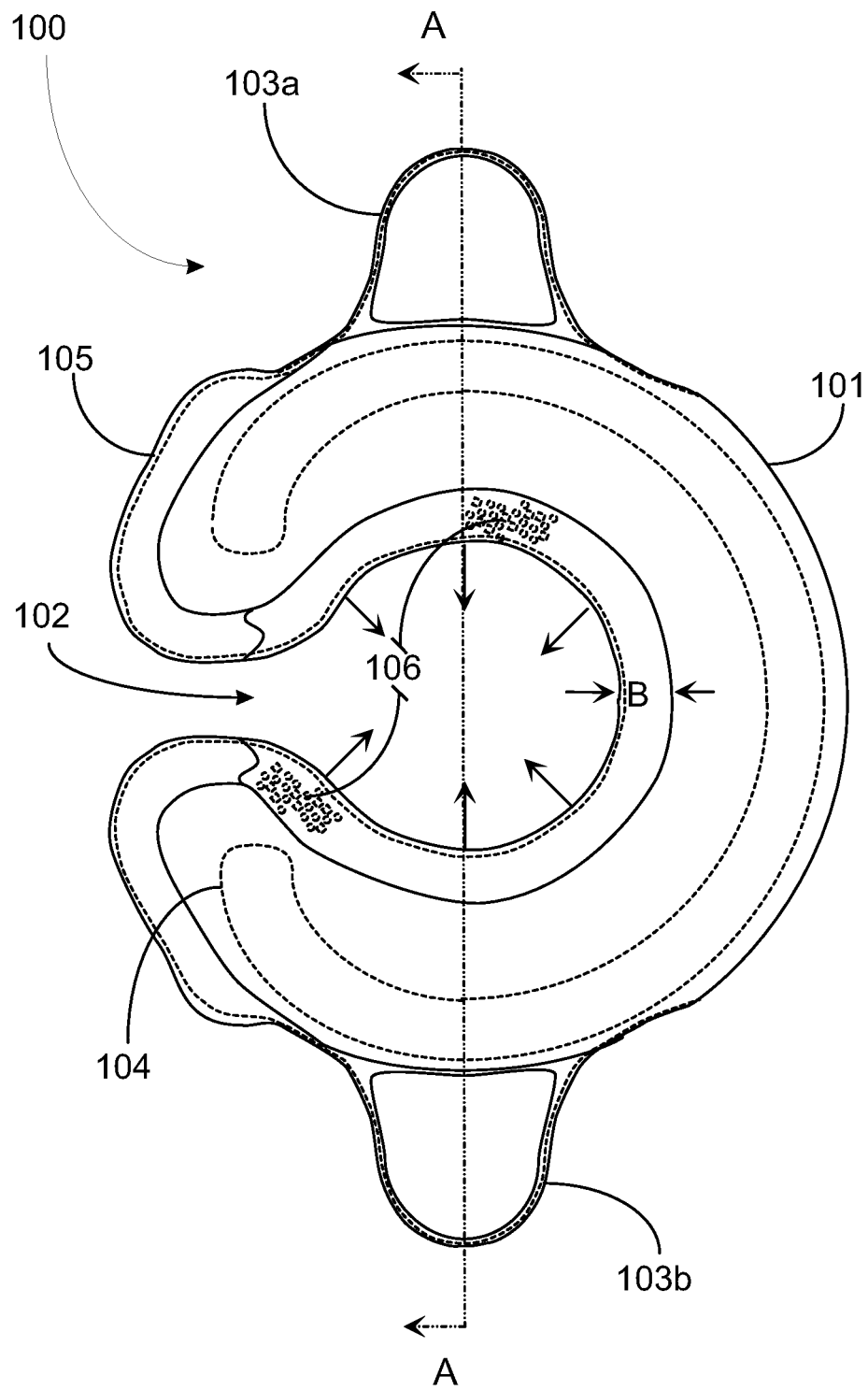
FIG. 1. is an elevation view of a silicone slow-occlusion apparatus according to an embodiment of the invention.

FIG. 1. is an elevation view of a slow-occlusion apparatus 100 according to an embodiment of the present invention. Slow-occlusion apparatus 100 may be crafted largely from medial grade silicone tubing of at least grade VI, which may be long term implantable in surgical procedures. One of the notable characteristics of the silicone is semi-permeability to water by osmosis.

Slow-occlusion apparatus 100 includes a plastic ring 104, shaped in a partial circle, encased in a silicone housing 101. Plastic ring 104 may be formed of a medical grade polyetheretherketone (PEEK) plastic. Plastic ring 104 is a rigid or semi-rigid plastic ring approximately 2 millimeters thick and 5 millimeters wide. Plastic ring 104 has a rectangular cross-section in this embodiment, and is approximately four fifths closed.

PEEK ring 104 is provided to maintain a semi-rigid structure that may prevent the occlusion apparatus from opening or widening due to the occlusion process which occurs over a period of time. The resiliency of the PEEK ring also provides for being able to open the apparatus to place the apparatus over a vessel to be occluded. In one embodiment, silicone tubing is placed over PEEK ring 104 and the tubing is closed off at both ends to encase the ring and define housing 101. Occlusion apparatus 100 in one embodiment may have approximately 6.5 millimeters outside diameter (OD) and a 5-millimeter ID lumen.

Occlusion apparatus 100 comprises a silicone bladder 105 in the form of a length of silicone tubing of a smaller diameter and wall thickness than encasement 101, cut to a length that sufficiently exceeds the circumferential length of the PEEK plastic ring. Bladder 105 is linearly attached to silicone encasement 101 around the inner diameter of encasement 101 defining a lumen region 102. The bladder tubing is fixed by adhesive to the encasement 101, forming the lumen diameter and extends out of the lumen and at least partly over the outside surface wall of encasement tubing 101. Bladder 105 may be attached to encasement 101 using a transparent or clear room-temperature-vulcanizing (RTV) silicone adhesive.

Apparatus 100 includes a pair of stirrups 103*a* and 103*b* positioned on opposite sides of the apparatus along a diameter orthogonal to a diameter passing through the gap in the apparatus. Stirrups 103*a* and 103*b* may comprise cut strips of fabric, such as Dacron fiber encased in silicone and glued in place on the outside of the occlusion apparatus, using RTV adhesive. Dacron strips provide sufficient support for manually expanding the ring using forceps or a hemostat device for placement of the occlusion apparatus over a blood vessel during a surgical implantation procedure. Other fabric and cord may be suitable. Apparatus 100 may be made translucent and radiolucent (invisible to X-rays) and may be left permanently over the occluded vessel.

Bladder 105 in one embodiment contains a mixture 106 of sodium chloride (NaCl), potassium chloride (KCl), and Polyacrylamide granules. The polyacrylamide granules swell into a hygroscopic gel-like substance when exposed to moisture, and the ratio of the salt mixture changes the hygroscopic strength of the apparatus, regulating the rate of absorption of water, and therefore the time period necessary for the lumen to close. Apparatus 100 contains no metals. The salts and polymer granules are isolated within the lumen portion of bladder 105 by pinching or otherwise closing off the rest of the lumen bladder tube at the location of the gap into lumen 102.

In general operation, apparatus 100 is placed over a small blood vessel that requires occlusion. Apparatus 100 is designed to fit over small vessels such as those no larger than 5 mm or 6 mm in outside diameter. However, larger and smaller apparatus may be manufactured for use with larger or smaller vessels. The operator manipulates the apparatus by using hemostats or forceps placed in stirrups 103*a* and 103*b* to expand the apparatus against resistance of the PEEK plastic ring, enough to place it over the vessel at a place in the vessel where occlusion is desired.

Once the apparatus is placed over a vessel, the forceps is released, the PEEK ring reverts to its original diameter, and the operator may close the surgery wound and leave the apparatus isolated in the patient. In the example of FIG. 1, bladder 105 is at rest and not inflated due to moisture osmosis. The original thickness B of the bladder may be approximately 1 to 2 or 3 millimeters. As the apparatus begins to take on surrounding moisture into the bladder section through osmosis through silicone walls, the bladder begins to swell as the polyacrylamide granules transform into hygroscopic gel. The swelling of the bladder lining within the lumen of the apparatus is constrained to close the lumen against the resistance of the PEEK ring. The lumen closes the blood vessel slowly over a considerable period of time (6 weeks) to prevent potential portal hypertension.

Figure 2:
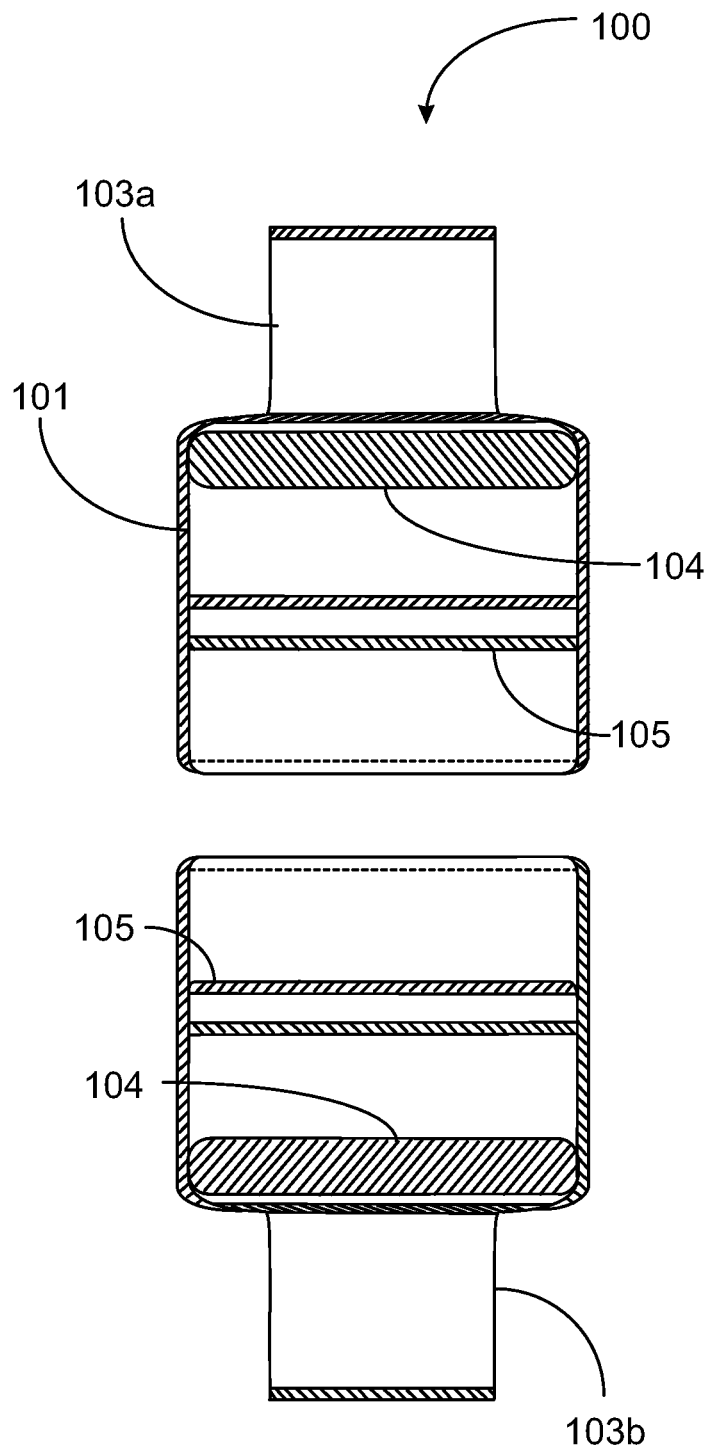
FIG. 2 is a sectioned view of the slow-occlusion apparatus of FIG. 1 taken along section line A-A.

FIG. 2 is a sectioned view of slow-occlusion apparatus 100 of FIG. 1 taken along section line A-A. Apparatus 100 is seen in section view from a center line perspective depicting Dacron stirrups 103*a* and 103*b* at opposite side of the apparatus, orthogonal to the direction of the gap into the lumen region of the apparatus. Each stirrup may be approximately 2 to 4 millimeters wide and perhaps a millimeter or less in thickness, although these dimensions may vary in alternative embodiments. The openings formed through hemostat stirrups 103*a* and 103*b* are sufficiently large to enable use of hemostats or forceps to handle the apparatus and to spread the apparatus to apply over a vessel to be occluded.

Dacron is favored by the inventor in a preferred embodiment for stirrups 103*a* and 103*b* because of its inherent strength, however other materials might be used in substitution therefor without departing from the spirit and scope of the present invention. The Dacron strips are sufficiently long as to leave enough material at either end of the stirrup to glue down to the outside of the silicon encasement 101. PEEK ring 104 provides a semi-rigid annular structure functioning as a backbone support to prevent the apparatus from opening when bladder 105 is expanding toward the center of the apparatus against the blood vessel outer wall. However, PEEK ring 104 is sufficiently flexible such that the ring may be expanded by hemostat or forceps used in conjunction with stirrups 103*a* and 103*b* to put the apparatus in place around a blood vessel.

Encasement tubing 101 completely encloses PEEK ring 104 and may be completely hollowed apart from wall thickness. In one embodiment, rectangular tubing may be used to enclose PEEK ring 104. The silicone tubing may have a consistent wall thickness such as with annular or elliptical tubing or a variable wall thickness as might be the case with some rectangular tubing. Bladder 105 has a footprint that extends significantly across the width of occlusion apparatus 100 in this example. In another embodiment, bladder 105 may be a small diameter annular or elliptical tubing that may occupy a smaller footprint than a rectangular tubing may occupy.

Figure 3:
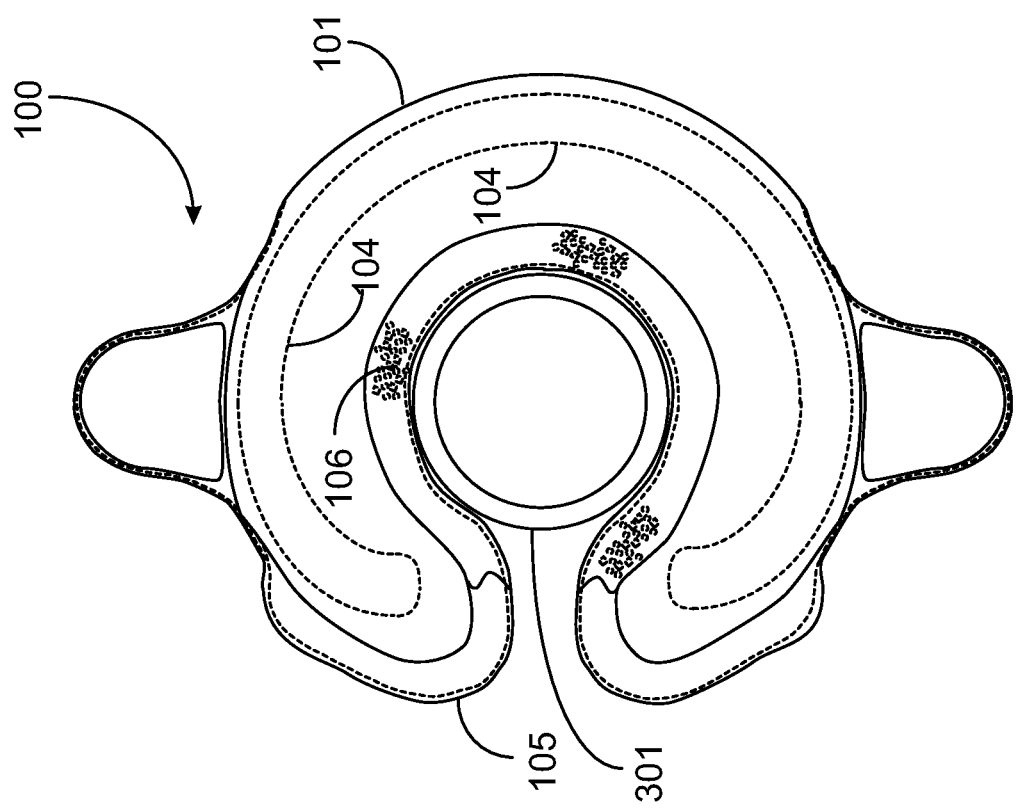
FIG. 3 is an elevation view of the slow-occlusion apparatus of FIG. 1 in an open state, positioned over a vessel to be occluded.

FIG. 3 is an elevation view of the occlusion apparatus of FIG. 1 in an open state positioned over a vessel 301 to be occluded. Forceps or a hemostat device may be used to open the apparatus and to place it over the vessel. In this example, the lumen is approximately 5 mm in diameter without expansion of bladder 105 in the lumen area. Ring 104 provides a sturdy backbone structure to prevent the apparatus from expanding or otherwise lifting off the blood vessel.

Mixture 106 is depicted within the bladder, confined to the area of the bladder occupying the lumen of the apparatus. It may be assumed that the mixture of salt and poly granules may be dispersed evenly throughout the bladder to achieve an even swelling of the bladder. However, even swelling of the bladder is not absolutely required as long as the vessel occludes properly over the time period allotted for the occlusion process to complete. The time period may be defined as the time it takes for the dry mix in the bladder to become saturated enough to begin swelling and continue to expand until the vessel is closed.

Moisture enters the bladder by osmosis through the membrane (wall) of the bladder. As the dry mixture becomes wet the polyacrylamide granules become a gel that continues to slowly expand due to continued exposure to the moisture. The rate of expansion is partly controlled by the amounts of NaCl and KCl in the mix relative to the polymer, and partly be the permeability characteristics of the silicone used.

Figure 4:
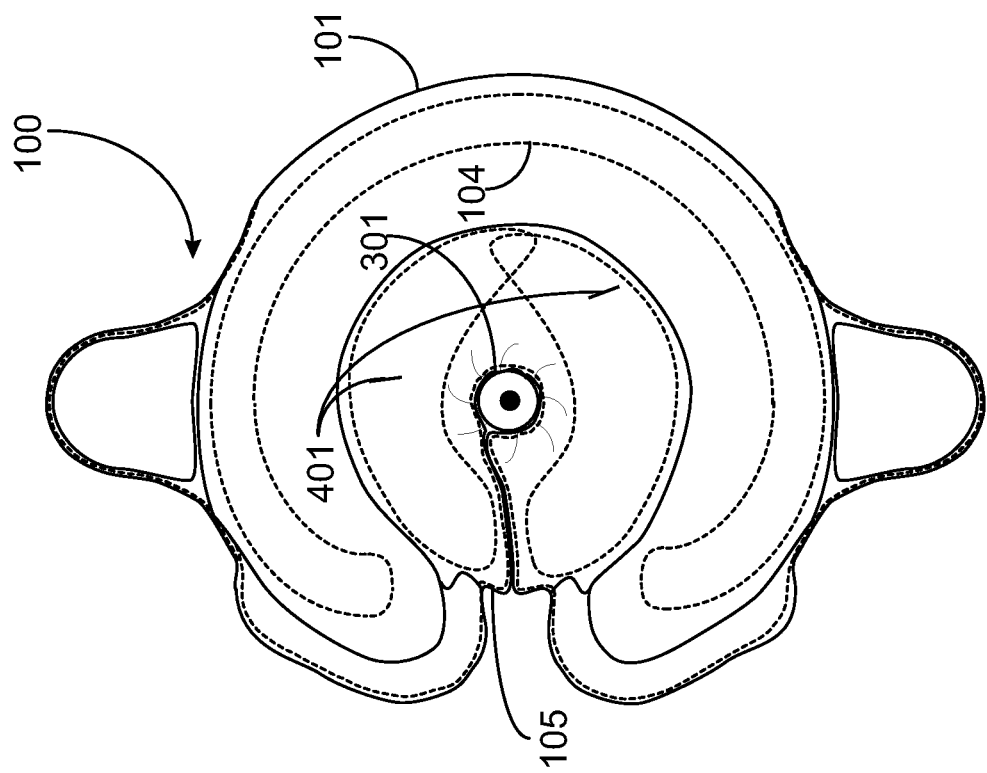
FIG. 4 is an elevation view of the occlusion apparatus of FIG. 1 in a closed (occluded) state over a vessel.

FIG. 4 is an elevation view of occlusion apparatus 100 of FIG. 1 in a closed (occluded) state over a blood vessel. Occlusion apparatus 100 is in a closed state in this example, presumably several weeks after implanted. Mixture 106 has transferred into a gel through osmosis and has continued to swell slowly. Gel 401 represents mixture 106 after about 6 weeks of absorbing water. Prior art devices occlude due to fibrosis and or thrombosis. However, these processes may vary widely relative to time in closing a vessel. The prescribed time period for occlusion in the present invention is an arbitrary 6-week period. The ratio of salts to polyacrylamide crystals in mixture (106) is key to the time period for closing the vessel and that time period may be adjusted by adjusting the ratio of the organic and inorganic salts used relative to the amount of polyacrylamide crystals.

The expansion of gel 401 causes bladder 105 to close over blood vessel 301 to the point of occlusion wherein the vessel vestiges and is eventually eliminated. Bladder 105 is closed off at the ring gap to isolate the absorbent mixture of salt and polyacrylamide into the lumen area covering the vessel. The portion of the bladder tubing extending out beyond the lumen region on either side of the encasement silicone provides support to the inflated portion of the bladder, which is the isolated section ringing the lumen.

Figure 5:
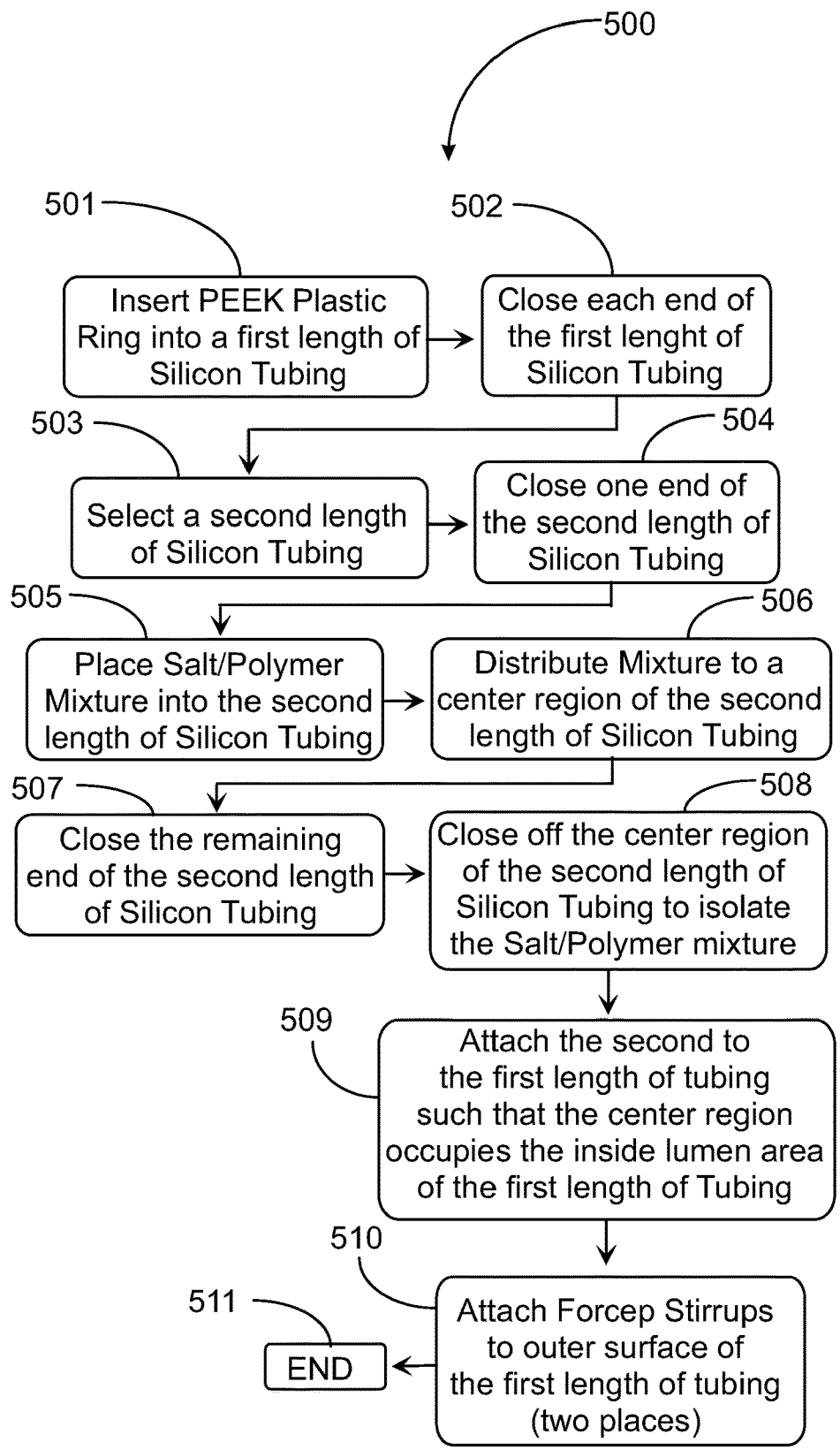
FIG. 5 is a process flow chart depicting steps for assembling the slow-occlusion apparatus of FIG. 1.

FIG. 5 is a process flow chart depicting steps for assembling the slow-occlusion apparatus of FIG. 1. At step 501 a user may insert a PEEK plastic ring analogous to ring 104 of FIG. 1 into a first length of silicone tubing. The silicone tubing may be rectangular, annular, oblong, or elliptical without departing from the spirit and scope of the present invention. The length of the silicone tubing is greater than the length of the plastic ring. At step 502 the user may close each end of the first length of the silicone tubing such as by using an RTV adhesive. At step 503, the user may select a second length of silicone tubing to form a bladder piece. The second length of tubing is significantly longer than the inside diameter of the first length of tubing installed over the plastic ring in step 501 and 502, such that the ends extend out of the lumen and over the outside surface of the encasement silicone, which is the first length of tubing.

It is noted herein that the second length of tubing is significantly smaller in diameter or height and width (rectangular) than the first length of tubing, however the selected size must be able to expand toward center point of the lumen such that the vessel will eventually be occluded. At step 504, the user may close one end of the second length of silicon tubing.

At step 505, the user may place a specified ratio and amount of a slat/polymer mixture, more particularly, NaCl/KCl/Polyacrylamide granules into the second length of tubing through the open end. At step 506, the user may distribute or otherwise dispose the mixture to a marked center region of the second length of tubing that would be sufficiently long enough to cover the lumen of the apparatus. At step 507 the user may close the remaining open end of the second length of tubing. At step 508 the user may close off or pinch to close the center region at its marked boundaries to isolate the mixture in the center section of the second length of silicone tubing.

It may be noted herein that in one aspect the user may first close the second length of tubing at a first boundary of a center section, may insert the mixture through the end having access to the center section, and then close off the second boundary of the center section of the tubing. At this point the user may then close both ends of the second length of tubing.

At step 509, the user may attach the second length of silicone tubing to the first length of silicone tubing such that the center section or region containing the salt/polymer mix occupies the inside lumen area of the first length of tubing. An RTV glue may be used to attach the bladder (second length). The user may attach the forceps stirrups or seats to the outer surface of the first length of tubing at two places (stirrups) disposed opposite of one another with the alignment thereof roughly orthogonal to the horizontal center line of the ring gap.

It will be apparent to one with skill in the art that the slow-occlusion apparatus of the invention may be provided using some or all of the described features and components without departing from the spirit and scope of the invention. It will also be apparent to the skilled person that the embodiments described above are specific examples of a single broader invention that may have greater scope than any of the singular descriptions taught. There may be many alterations made in the descriptions without departing from the spirit and scope of the present invention. The invention is limited only by the breadth of the claims below.

The invention claimed is:

1. A method for occluding a blood vessel, comprising steps of:
   encasing a semi-rigid, circular plastic ring, open at one point of a circumference, in silicon material;
   forming a bladder along an inside diameter of the silicon material encasing the plastic ring;
   placing a mixture of sodium and potassium salts and polyacrylamide granules in the bladder, and closing and sealing the bladder;
   forming a pair of opposed stirrups on an outside diameter of the silicon material encasing the plastic ring;
   spreading the encased plastic ring by the stirrups to an extent that an opening is accomplished through the ring of an extent enabling the ring to be placed over a blood vessel to be occluded;
   placing the encased plastic ring over the blood vessel;
   releasing the stirrup, allowing the ring and bladder to close around the blood vessel, such that the bladder, constrained by the ring from expanding outward, absorbing moisture by osmosis over time, expands inward, and over a time t fully occludes the blood vessel.

2. The method of claim 1 wherein the ratio amounts of materials in the silicone bladder change time t.

3. The method of claim 2 wherein the ratios are controlled to result in t=six weeks.

4. The method of claim 1 wherein the blood vessel is a portosystemic shunt.

* * * * *